(12) United States Patent
Rugnone

(10) Patent No.: US 10,927,012 B2
(45) Date of Patent: Feb. 23, 2021

(54) PROCESS AND SYSTEM TO CAPTURE AMMONIA FROM A PURGE GAS OF A UREA PLANT

(71) Applicant: Casale SA, Lugano (CH)

(72) Inventor: Luca Rugnone, Como (IT)

(73) Assignee: Casale SA, Lugano (CH)

(*) Notice: Subject to any disclaimer, the term of this patent is extended or adjusted under 35 U.S.C. 154(b) by 0 days.

(21) Appl. No.: 16/485,276

(22) PCT Filed: Feb. 1, 2018

(86) PCT No.: PCT/EP2018/052477
§ 371 (c)(1),
(2) Date: Aug. 12, 2019

(87) PCT Pub. No.: WO2018/153630
PCT Pub. Date: Aug. 30, 2018

(65) Prior Publication Data
US 2019/0375649 A1  Dec. 12, 2019

(30) Foreign Application Priority Data
Feb. 27, 2017 (EP) .................................. 17158199

(51) Int. Cl.
*B01D 53/14* (2006.01)
*C01C 1/12* (2006.01)
*C01C 1/26* (2006.01)

(52) U.S. Cl.
CPC ............ *C01C 1/12* (2013.01); *B01D 53/1493* (2013.01); *C01C 1/26* (2013.01); *B01D 2252/103* (2013.01)

(58) Field of Classification Search
CPC ........ B01D 53/74; B01D 53/76; B01D 53/58; C07C 273/02; C07C 273/04; C07C 273/14; C07C 273/16
See application file for complete search history.

(56) References Cited

U.S. PATENT DOCUMENTS

| | | | | | |
|---|---|---|---|---|---|
| 3,725,210 | A | * | 4/1973 | Otsuka | C07C 273/16 203/42 |
| 6,084,129 | A | * | 7/2000 | Romiti | C07C 273/04 504/327 |
| 2012/0240649 | A1 | * | 9/2012 | Meessen | B01D 53/80 71/30 |
| 2012/0330060 | A1 | * | 12/2012 | Eliasson | B01D 53/58 564/67 |
| 2018/0362452 | A1 | * | 12/2018 | Rugnone | B01D 3/009 |

FOREIGN PATENT DOCUMENTS

| | | | | | |
|---|---|---|---|---|---|
| CA | 2 774 246 | C | * | 6/2016 | ............ B01D 53/54 |
| CN | 101918115 | A | * | 12/2010 | ........... C07C 273/16 |
| CN | 107459372 | A | * | 12/2017 | ........... C07C 273/02 |
| EP | 0 891 968 | A1 | | 1/1999 | |

OTHER PUBLICATIONS

International Search Report and International Preliminary Report on Patentability issued in connection with PCT/EP2018/052477.

* cited by examiner

*Primary Examiner* — Timothy C Vanoy
(74) *Attorney, Agent, or Firm* — Akerman LLP

(57) ABSTRACT

A process and system for removing ammonia from ammonia-containing purge gas of a urea plant, the process comprising: contacting said ammonia-containing purge gas with carbon dioxide at a low temperature, reaction of ammonia to form crystals of ammonium salts in a multiphase stream, and removal of the solid ammonium salts from the multiphase stream.

21 Claims, 2 Drawing Sheets

United States Patent US 10,927,012 B2

PROCESS AND SYSTEM TO CAPTURE AMMONIA FROM A PURGE GAS OF A UREA PLANT

This application is a national phase of PCT/EP2018/052477, filed Feb. 1, 2018, and claims priority to EP 17158199.4, filed Feb. 27, 2017, the entire contents of both of which are hereby incorporated by reference.

FIELD OF THE INVENTION

The invention relates to the field of the synthesis of urea and discloses a process and system for removing ammonia from the purge gas of a urea plant.

PRIOR ART

Urea is synthesized by reacting ammonia and carbon dioxide at high temperature and pressure. An overview of the industrial synthesis of urea can be found in the Ullmann's Encyclopedia of Industrial Chemistry, Wiley-VCH Verlag.

Typically, a urea plant comprises a high pressure synthesis section, a recovery section, a section for vacuum evaporation and water treatment and a finishing section. The synthesis section comprises a urea synthesis reactor and may further comprise a stripper and a condenser working at synthesis pressure in a so-called high-pressure synthesis loop.

The synthesis section produces an aqueous solution of urea containing unconverted ammonium and carbon dioxide, which is treated in the recovery section to recover the unconverted reagents in the form of a recycle solution commonly named ammonium carbamate solution, which is sent back to the synthesis section. A concentrated urea solution obtained in the recovery section is further concentrated in the vacuum evaporation section to get a urea melt or a highly concentrated solution. The finishing section processes said melt or solution to obtain a solid urea product in the form of prills or granules.

An issue of the known urea plant concerns the treatment of the purge gas. A purge gas is extracted for example from one or more equipment of any of the above mentioned synthesis section, recovery section and vacuum evaporation section.

Extraction of purge gas stream(s) is necessary in order to avoid accumulation of inert gas which, by definition, do not participate to the synthesis reactions. Moreover inert gas are detrimental to the conversion of reactants into urea. In particular, the reactor performance is highly affected by the accumulation of such inert gas.

The inert gas may include one or more of nitrogen, oxygen, methane, argon and hydrogen, which enter the system as impurities contained in the carbon dioxide feed. The inert gas may further contain air or pure oxygen introduced into the reactor (e.g. added to the carbon dioxide feed) for passivation.

The purge gas inevitably contains also some gaseous ammonia and carbon dioxide. It has to be noted that a urea process requires some excess of ammonia and ammonia is a highly volatile compound which is easily entrained in the vented gas.

The presence of carbon dioxide and ammonia in the purge gas poses a number of problems. First, it is not desirable to subtract such gaseous reactants from the system; second, the release into atmosphere of carbon dioxide and ammonia should be limited or avoided. This is particularly the case of ammonia which is a toxic gas and a known source of pollution. In some sites, the applicable law requires ammonia emissions to atmosphere to meet stringent limitation, e.g. less than 100 ppm.

The prior art techniques to control the ammonia emissions include washing the ammonia-containing purge gas with water or with an acid, or flaring the purge gas. However they introduce some drawbacks.

The washing with water has the drawback of producing a dilute aqueous solution of ammonia which cannot be freely discharged to environment and is normally recovered in the urea plant, for example in the recovery section. However introducing additional water in the process is not desirable because water would shift the equilibrium against the formation of urea. Furthermore, water washing alone is generally not able to reach the required low content of ammonia in the gas.

Acid washing is more effective in the removal of ammonia and can reach a residual content of 100 ppm or less. However it requires expensive equipment and generates large amounts of an aqueous solution containing a salt of ammonia such as ammonium nitrate or ammonium sulfate, which must be displaced somehow. A direct utilization of this solution is possible only in a site for integrated production of urea and urea-ammonium nitrate (UAN) or sulfate. If the urea site does not provide production of such nitrate or sulfate, the by-product solution of the acid washing is a problem.

The flaring technology provides that the inert stream is added with a support fuel such as methane and combusted in order to burn all the ammonia. This technology is nowadays obsolete and has the drawback of requiring a fuel and generating nitrogen oxides which must be removed in a dedicated de-NOx unit, which is very expensive.

EP 0 891 968 discloses a process for reducing the residual free ammonia emissions from a urea production plant including the addition of carbon dioxide to the urea melt.

SUMMARY OF THE INVENTION

The invention aims to solve the above drawbacks of the prior art. The invention in particular aims to providing an efficient and cost-effective system for removing ammonia from the inert-gas containing purge gas vented from a urea plant.

These aims are reached with a process for removing ammonia from ammonia-containing purge gas of a urea plant according to the claims. Further preferred features of the invention are stated in the attached dependent claims. An aspect of the invention is also an ammonia capture system according to the claims.

The inventive process comprises that ammonia-containing purge gas is brought into direct contact with carbon dioxide and refrigeration is provided in order to obtain a refrigerated mixed stream. At least some of the ammonia in the purge gas reacts to form one or more ammonium salts and a multiphase mixed stream containing the ammonium salts is thus obtained.

Refrigeration is provided by at least one of:
refrigeration of the ammonia-containing purge gas prior to contacting said stream of carbon dioxide,
refrigeration of said stream of carbon dioxide prior to contacting the ammonia purge-gas,
refrigeration of the mixture of purge gas and carbon dioxide.

Said ammonia-containing purge gas may comprise a single stream or a plurality of streams vented from different sections of said urea plant. In a preferred embodiment, different vent streams are collected in a main header and the resulting stream is processed according to the invention.

The carbon dioxide is preferably gaseous. In some embodiments however the carbon dioxide may be at a low temperature and carbon dioxide may liquefy. The liquid mole fraction in the carbon dioxide, if any, is preferably not greater than 0.1.

The mixed stream containing the one or more solid ammonium salts has a temperature preferably less than 10° C. (283 K), more preferably in the range 10 to −30° C. (283 to 243 K) and more preferably at ambient pressure or higher, preferably in the range 1 to 10 bar absolute, more preferably 1 to 2 bar absolute.

According to various embodiments of the invention, said mixed stream may involve two phases, i.e. solid and gas, or three phases, namely solid, liquid and gas. The ammonia contained in the purge gas is separated as ammonium salts in the solid phase.

According to first embodiments, the ammonia-containing purge gas is contacted with cold carbon dioxide, i.e. refrigeration is provided by the carbon dioxide itself. Preferably the cold carbon dioxide is in gaseous state.

According to second embodiments, refrigeration is provided by a further refrigerant medium. For example, in a preferred embodiment, a suitable refrigerant medium is added to the mixture of purge gas and carbon dioxide. The refrigerant medium is preferably a suitable solvent with a low solubility of ammonia and carbon dioxide. More preferably the solvent is organic oil.

According to third embodiments, the ammonia-containing purge gas is refrigerated before mixing with the carbon dioxide.

The above embodiments may be combined, i.e. two or more techniques for refrigeration may be implemented to reach a target temperature.

The invention provides de-sublimation of ammonia from the gas phase to a solid phase mainly according to the following equilibrium reactions:

$$NH_3(g)+CO_2(g)+H_2O(g)\leftrightarrows NH_4HCO_3(s) \quad (1)$$

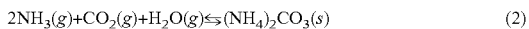

$$2NH_3(g)+CO_2(g)+H_2O(g)\leftrightarrows (NH_4)_2CO_3(s) \quad (2)$$

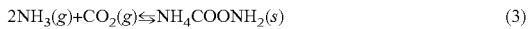

$$2NH_3(g)+CO_2(g)\leftrightarrows NH_4COONH_2(s) \quad (3)$$

wherein $NH_4HCO_3$ is solid ammonium bicarbonate; $(NH_4)_2CO_3$ is solid ammonium carbonate; $NH_4COONH_2$ is ammonium carbamate; (s) denotes solid and (g) denotes the gas phase.

Depending on conditions the ammonium salts can be in the hydrated form, bonded with one or more water molecules, for instance $(NH_4)_2CO_3$ x $2H_2O$ (dehydrate ammonium carbonate). Under the usual temperature and pressure of extraction of the purge gas, said purge gas phase is stable in the gaseous phase i.e. the equilibrium of reactions (1) (2) and (3) is strongly shifted towards the products which are all in a gas phase.

The additional amount of carbon dioxide, which is a reagent in the above reactions, determines a consumption of the ammonia contained in the purge gas because ammonia becomes the limiting reagent. The purge gas is preferably saturated with carbon dioxide.

Furthermore since the carbon dioxide is a reagent in all reactions, it reduces the partial pressure of free ammonia gas at the equilibrium. This effect is based on Le Chatelier's principle, according to which increasing the concentration of a reagent (CO2) in a chemical reaction will increase the concentration of products (the ammonium salts) by consuming additional co-reagent (NH3).

In the first embodiments where the process is refrigerated by cold carbon dioxide, the contact of the purge gas with the cold CO2 results in the formation of solid ammonium salts dispersed in a gas phase. The gas phase includes inert gas and excess carbon dioxide.

The flow rate and/or temperature of the cold carbon dioxide are regulated in order to keep the temperature of the mixed stream within a target range, for example less than 10° C. (about 283 K) and more preferably in the range of 10 to −30° C. (283 to 243 K).

The cold carbon dioxide, in order to provide refrigeration, has a temperature lower than the input purge gas. In preferred embodiments, the temperature of said cold carbon dioxide is equal to or less than 10° C. below zero (263 K), preferably in the range of 25 to 65° C. below zero (248 to 208 K).

The addition of cold CO2 drops the temperature shifting the reactions (1), (2) and (3) to the right side and promoting the formation of solid ammonium salts. The mixed stream obtained after contact with the cold carbon dioxide is a multi-phase stream containing a gaseous phase, depleted of ammonia and mainly composed of inert gas, and a solid phase containing de-sublimated ammonia.

In the second embodiments where the process is refrigerated by a solvent, the contact of ammonia and carbon dioxide, together with the cold solvent, results in the formation of solid ammonium salts dispersed in the solvent.

In an embodiment, carbon dioxide at ambient temperature and ambient pressure is mixed with the ammonia containing purge gas in a contacting equipment (absorber) where a cold organic oil is injected. The contacting equipment is preferably a column with packing or trays. A slurry containing ammonium salts dispersed in the solvent oil is thus formed. The ammonium salts are separated from the slurry by means of a filter and safely disposed, while the solvent is recycled to the absorber being first cooled in a dedicated heat exchanger working as cryostat.

In the third embodiments, the purge gas is suitably refrigerated. This can be made for example in a suitable heat exchanger (also termed cryogenic heat exchanger) with a cooling medium.

In all the embodiments of the invention, the amount of residual free ammonia in the gas phase of the mixed stream is very low, for example few ppm. The solid phase can be removed totally or partially from the mixed stream, according to the capacity of a respective phase separation device. Preferably all or substantially all the solid phase is removed.

The solid phase containing ammonia can be captured with inexpensive techniques e.g. by means of a filter or scrubber. Due to the very low residual free ammonia in the gas phase, a substantially ammonia-free gas is obtained.

A further advantage is that the process of the invention can accept higher ammonia load compared to the conventional systems such as washing. Yet a further advantage is that the captured ammonia can be recycled after washing into the urea process without introducing a too large amount of water or as alternative the ammonium salts can be separated and disposed as solid eliminating the need to recycle to the urea process.

Cold $CO_2$ can be provided, in a urea plant, at a low cost. For example a urea plant normally has a $CO_2$ feed which is compressed to synthesis pressure by means of an inter-refrigerated multi-stage compressor and, according to some embodiments, the carbon dioxide for the present process is taken from an intermediate refrigeration stage of said compressor and is expanded to reach the required low temperature. The expansion is preferably a free expansion without extraction of work, e.g. in a let-down valve. Preferably the expansion is such to avoid formation of liquid carbon dioxide, or limit the formation of such liquid to a small amount.

In a preferred embodiment, a secondary stream of carbon dioxide is taken from an inter-refrigeration stage at a pressure of 65 to 85 bar and, after cooling, is expanded to atmospheric pressure. Said secondary carbon dioxide stream normally comprises about 1% to 10%, preferably 1% to 5%, of the total carbon dioxide feed.

The embodiments using a refrigerant other than the carbon dioxide do not require a dedicated cold CO2 stream. These embodiments may be preferred, for example, when an additional amount of CO2 is not available or not convenient for some reasons, for example due to limited capacity of the available compressor.

The process of the invention may receive the purge gas as such, i.e. as it is vented from the urea plant. The process of the invention, however, can also be implemented in series with at least another process step to remove ammonia from the purge gas. Said at least another process step may be a conventional one, such as acid scrubbing or a flaring technology. According to some embodiments, a purge gas extracted from a urea plant is subjected to at least one treatment step removing some ammonia, and the so obtained ammonia-depleted purge gas is treated with the process of the invention to remove further ammonia.

The process of the invention, possibly in series with one or more further steps of removing ammonia, can reach a very low residual content of ammonia, thus approaching the ideal of "zero emission urea plant". Said residual content is typically less than 50 ppm and may reach 10 ppm or less in some embodiments.

An ammonia capture system according to the invention comprises:
a mixing device wherein said ammonia-containing purge gas and a stream of carbon dioxide are introduced,
at least one of a refrigerator for the ammonia-containing purge gas, a refrigerator for said stream of carbon dioxide, means to add a refrigerant medium to said mixing device,
the mixing device delivering a multiphase mixed stream containing solid ammonium salts, as a result of mixing and refrigeration of the purge gas and carbon dioxide, and
a phase-separation device disposed to receive said mixed stream from the mixing device and adapted to remove said ammonium salts from said mixed stream.

Preferably said mixing device includes a mixer or an ejector.

Preferably said phase-separation device comprises a solid-gas filter or a scrubber.

A refrigerator for the ammonia-containing purge gas is preferably a heat exchanger for indirect heat exchanger with a cooling medium.

A refrigerator for the carbon dioxide is preferably an expander, wherein the temperature is lowered by lowering the pressure of the carbon dioxide.

The invention is also applicable to revamping of urea plants. In the case of a revamped urea plant, the capacity may be increased and, consequently, the ammonia released in the vent gas is also increased. Hence the ammonia in the vent gas may be beyond the capacity of the existing capture system, if any.

An ammonia capture system according to the invention can replace, or can be added to, the existing capture system in order to cope with the increased amount of ammonia to be removed.

For example in some embodiments an ammonia capture system according to the invention is installed downstream an existing ammonia capture system, which means the newly-installed system of the invention receive the ammonia-depleted gas effluent from the existing system.

The invention is applicable to the known urea plants without restrictions, e.g. the invention is applicable to once-through urea plants, partial-recycle urea plants, total-recycle urea plants, stripping urea plants.

The advantages will emerge even more clearly with the aid of the description below, relating to a preferred embodiment.

DETAILED DESCRIPTION

Figure 1:
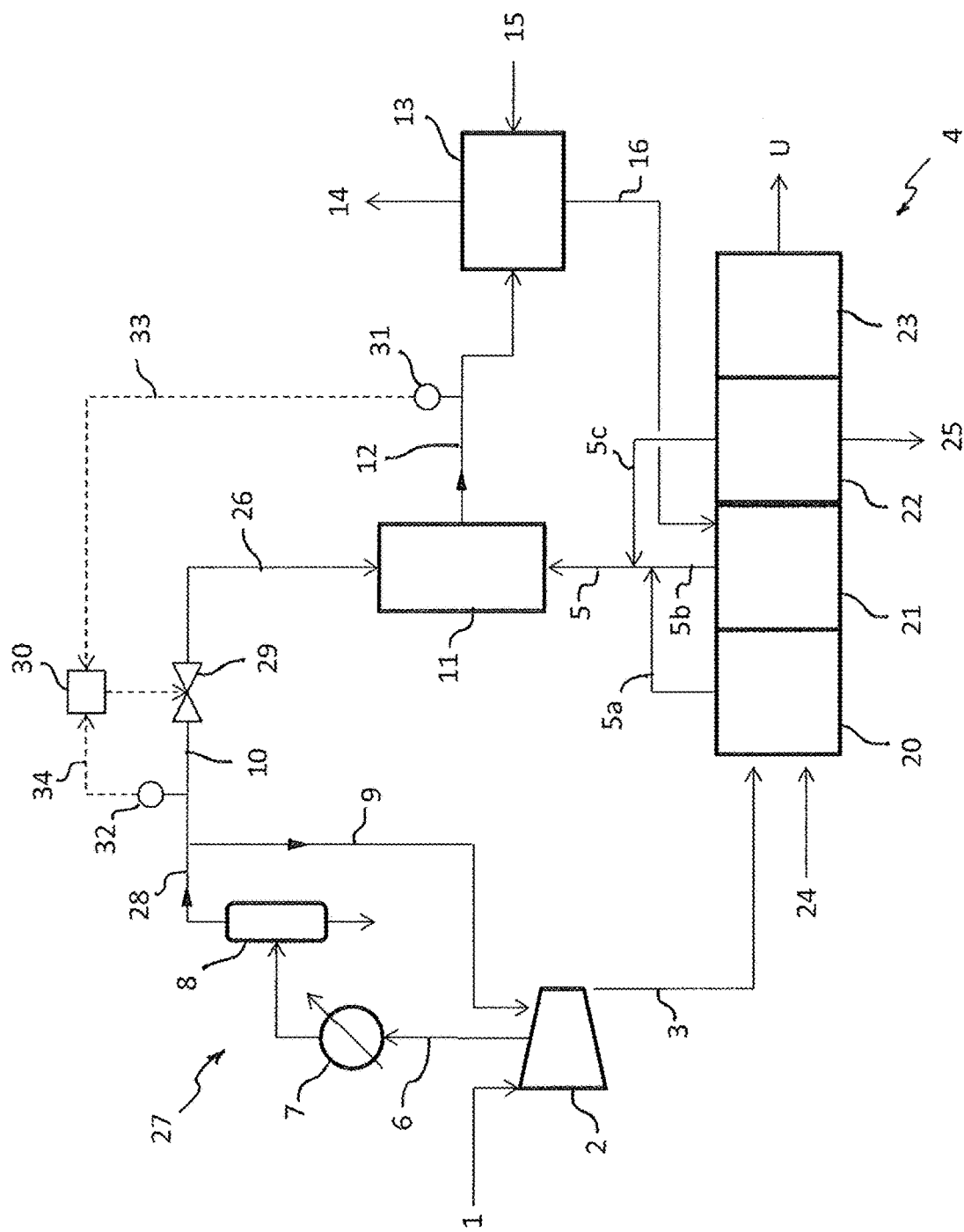
FIG. 1 is a scheme of a urea plant including an ammonia capture system according to a first embodiment of the invention.

Referring to FIG. 1, a carbon dioxide feed 1 is elevated to urea synthesis pressure in a multi-stage compressor 2 and the resulting compressed CO2 stream 3 is fed to a urea plant 4.

The urea plant 4 includes a synthesis section 20, a recovery section 21, an evaporation section 22 and a finishing section 23. The urea plant 4 also receives an ammonia feed 24 and delivers a urea product U. Some water 25 is discharged by the evaporation section 22.

Purge gas streams 5a, 5b and 5c are vented from said sections 20, 21 and 22 respectively and are collected in a stream 5. The purge gas 5 contains inert gases such as nitrogen, oxygen, methane, argon and hydrogen, and further contains some ammonia.

The ammonia-containing purge gas 5 is blended in a mixer 11 with a cold gaseous carbon dioxide 26 at a suitable low temperature resulting in the formation of a mixed stream 12 containing a solid phase of crystals of ammonium salts dispersed in a gaseous phase. Said crystals are mainly formed due to the change in the equilibrium of reactions (1) and (2) and (3) mentioned above, which is a consequence of the intimate mixing with the cold CO2. In some embodiments the stream 26 may contain a small liquid fraction.

The solid ammonia salts are removed from the stream 12 in a solid scrubber 13 wherein clean water 15 is injected, preferably cyclically (semi-continuous operation). The ammonia salts are dissolved in water and leave the scrubber 13 with an aqueous stream 16. The aqueous stream 16 can be recycled to the urea plant 4, for example to the recovery section 21.

The gas 14 which emerges from the scrubber 13 is substantially ammonia-free. As stated above, only few ppm of free ammonia remain in the mixed stream 12 and therefore, after removal of the solid ammonia salts, a gaseous phase practically free of ammonia is obtained. For example said gas 14 contains less than 10 ppm ammonia and preferably around 5 ppm.

Recycle of the aqueous stream 16 to the urea plant is advantageous since it reduces the total clean water amount needed for the ammonia scrubbing. Also, the amount of water introduced in the urea plant 4 is smaller compared to water washing of the prior art. In some embodiments the solid ammonium salts can be displaced and disposed safely with no recycle to the urea process.

The scrubber 13 can be replaced in other embodiments by another phase-separation device suitable to separate the solid phase and gaseous phase of the mixed stream 12. In some embodiments said phase-separation device may include a filter.

The generation of the cold carbon dioxide 26 is now described in accordance with a preferred embodiment.

Said cold carbon dioxide 26 is obtained from an inter-refrigeration stage 27 of the compressor 2. Preferably the inter-refrigeration stage 27 is between the last two stages of compression.

The inter-refrigeration stage 27 comprises essentially a refrigerator 7 and a phase separator 8. A carbon dioxide 6 taken from an intermediate stage of the compressor 2 passes through the refrigerator 7 and then the separator 8.

A major portion 9 of the carbon dioxide 28 emerging from the separator 8 is reintroduced to the next stage of the compressor 2. A secondary stream 10 is separated and expanded to a much lower pressure (e.g. atmospheric pressure) through a let-down valve 29. The temperature of the gaseous CO2 drops substantially, due to the free expansion through said valve 29, thus obtaining the cold carbon dioxide 26.

In a variant embodiment the secondary stream 10 can be separated after the refrigerator 7 but before the phase separator 8.

The valve 29 is preferably close to the inlet of the mixer 11 to reduce the risk of ice formation due to residual moisture in the secondary stream 10.

Preferably the flow rate of said secondary stream 10 is regulated to keep the temperature of the mixed stream 12 within a target range. In FIG. 1 the flow rate through the valve 29 is controlled via a flow controller 30, a temperature probe 31 of the mixed stream 12 and a flow meter 32 of the carbon dioxide stream 10.

The flow controller 30 receives signals 33 and 34 from said temperature probe 31 and flow meter 32, corresponding to the temperature of the stream 12 and current flow rate of cold carbon dioxide directed to the mixer 11. Based on these signals, the flow controller 30 adjusts the flow rate of the carbon dioxide directed to the mixer 11, in order to keep the temperature of the mixed stream 12 within a desired range suitable for the de-sublimation of ammonia.

Figure 2:
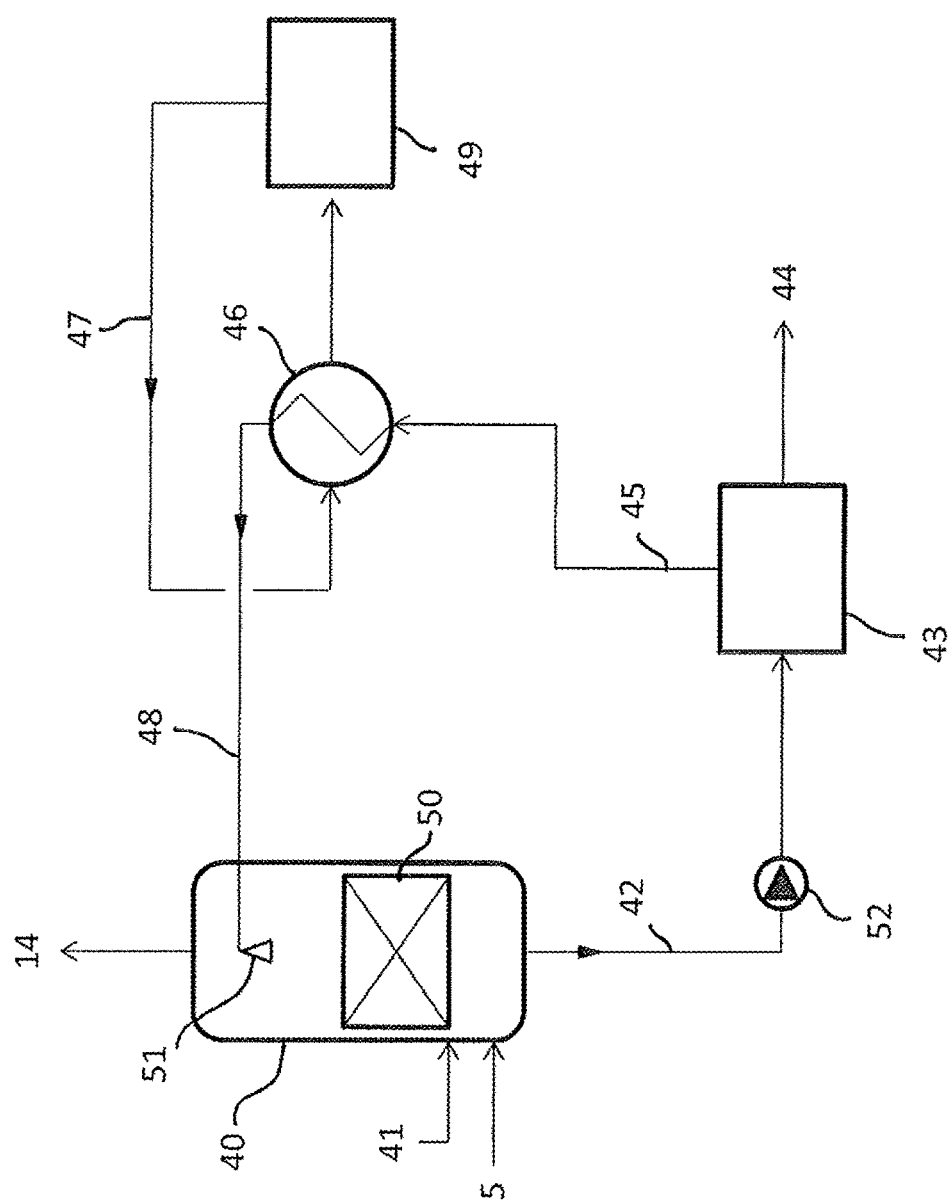
FIG. 2 is a scheme of a second embodiment of the invention.

FIG. 2 illustrates a second embodiment of the invention.

The ammonia containing purge gas 5 and carbon dioxide 41 enter an absorber 40. Preferably the absorber 40 is a packed column, equipped with suitable packing 50 to enhance the heat and mass transfer among the phases.

The carbon dioxide 41 can be taken from the suction side of the compressor 2. The carbon dioxide 41 may be at atmospheric pressure.

A solvent 48 at low temperature (i.e. −10° C.), for instance an oil for low temperature service, is injected in the top of the absorber 40, e.g. with a sprayer 51, and contacts the mixture of purge gas 5 and carbon dioxide 41 in a counter-current arrangement.

The ammonia contained in the purge gas 5 and the carbon dioxide 1a react at low temperature forming ammonium salts. A multi-phase stream 42 comprising the ammonium salts dispersed in a solid-liquid slurry is withdrawn from bottom of the absorber 40. Said multi-phase stream 42 may also contain ice crystals originated by water contained in the streams 5 and 41.

The multi-phase stream 42 is fed by a suitable pump 52 to a filter 43 where ammonium salts are separated from the solvent. The ammonium salts including some ice crystals are safely disposed as stream 44.

The solvent is recycled via line 45 through a heat exchanger 46, resulting again in the cold solvent 48. In the heat exchanger 46, the temperature of the solvent is dropped by means of a suitable refrigerant 47 provided by a cryostat 49.

As in FIG. 1, a substantially ammonia-free gas 14 is withdrawn from top of the absorber 40.

EXAMPLES

Referring to FIG. 1, a total of 47 kmol/h of purge gas 5 are vented from a urea plant having a capacity of 1000 to 2000 MTD. Said gas 5 has a temperature of 30° C., a pressure of 1 bar, and contains (in volume) 93.2% of inert gas, 2.1% ammonia, 0.4% carbon dioxide, 4.3% water.

The CO2 stream 28 at 65 to 85 bar and 50° C. after refrigeration. The CO2 stream 10 is expanded to atmospheric pressure obtaining the cold carbon dioxide 26.

After mixing with 79 kmol/h of said cold carbon dioxide 26, the multi-phase stream 12 has a temperature of 5° C., a pressure of 1 bar, the gas phase contains: 62.9% CO2, 34.7% inert gas, 1.6% water and 0.8% nitrogen, ammonia negligible. All the ammonia is in the solid phase as ammonium salts.

The embodiment of FIG. 2 has generally a smaller flow rate than the previous embodiment. For example 20 kmol/h of carbon dioxide are enough to be added to 47 kmol/h of purge gas containing 2.1% of ammonia.

What is claimed is:

1. A process for removing ammonia from ammonia-containing purge gas of a urea plant, the process comprising:
    a) said ammonia-containing purge gas is contacted with a stream of carbon dioxide;
    b) at least one of:
        said ammonia-containing purge gas prior to contacting said stream of carbon dioxide,
        said stream of carbon dioxide prior to contacting the ammonia purge-gas,
        the mixture of purge gas and carbon dioxide resulting from the contacting step a),
        is refrigerated;
    c) in the so obtained refrigerated mixture of purge gas and carbon dioxide, at least some of the ammonia contained in the purge gas reacts to form one or more ammonium salts and a multiphase mixed stream containing the ammonium salts is obtained, and
    d) said ammonium salts are removed from said mixed stream.

2. The process according to claim 1, wherein said at least one of purge gas, carbon dioxide and mixture of purge gas and carbon dioxide is refrigerated to a temperature lower than the temperature of the input ammonia-containing purge gas.

3. The process according to claim 1, wherein said mixed stream has a temperature equal to or less than 10° C.

4. The process according to claim 3, wherein the ammonia-containing purge gas is contacted with said carbon dioxide at a pressure of 1 to 10 bar abs.

5. The process according to claim 4, wherein the ammonia-containing purge gas and the refrigerated carbon dioxide are contacted in a mixer or in a gas ejector.

6. The process according to claim 4, wherein the ammonia-containing purge gas is contacted with said carbon dioxide at a pressure of 1 to 2 bar abs.

7. The process according to claim 3, wherein said mixed stream has a temperature in the range of 10° C. to −30° C.

8. The process according to claim 1, comprising refrigeration of said carbon dioxide, wherein the temperature of refrigerated carbon dioxide is equal to or less than −10° C.

9. The process according to claim 8, wherein refrigerated carbon dioxide is obtained by: separating a secondary gaseous stream of carbon dioxide from an inter-refrigeration stage of a carbon dioxide feed compressor of said urea plant, and expanding said secondary stream of carbon dioxide to a lower pressure in order to lower its temperature.

10. The process according to claim 9, wherein said secondary stream of carbon dioxide has a pressure of 65 to 85 bar and a temperature after inter-refrigeration of 40 to 80° C., and is expanded to atmospheric pressure.

11. The process according to claim 8, comprising refrigeration of said carbon dioxide, wherein the temperature of refrigerated carbon dioxide is in the range −25 to −65° C.

12. The process according to claim 1, wherein during or after the contacting of ammonia-containing purge gas and carbon dioxide, a further refrigerant medium is added.

13. The process according to claim 12, comprising the steps of: contacting the ammonia-containing purge gas and the carbon dioxide in an absorber, and injecting said refrigerant medium into said absorber, so that the refrigerant medium comes into direct contact with the purge gas and carbon dioxide.

14. The process according to claim 12, wherein the refrigerant medium is at a temperature equal to or less than −10° C.

15. The process according to claim 1, wherein said ammonia-containing purge gas comprises a plurality of purge streams taken from different sections of said urea plant.

16. The process according to claim 1, wherein said ammonium salts include ammonium bicarbonate $NH_4HCO_3$ and ammonium carbamate $NH_4COONH_2$.

17. The process according to claim 1, wherein ammonium salts are removed from said mixed stream in a filter or by a scrubbing process.

18. The process according to claim 17, wherein said scrubbing process comprises water as a scrubbing medium.

19. The process according to claim 1, wherein the ammonia-containing purge gas is a purge gas as vented from the urea plant, or the process comprise at least one step of removing ammonia from the purge gas prior to said contacting with cold carbon dioxide.

20. The process according to claim 1, wherein said mixed stream contains a residual amount of free gaseous ammonia of less than 10 ppm.

21. An ammonia capture system for removing ammonia contained in a purge gas of a urea plant, comprising:
a mixing device wherein said ammonia-containing purge gas and a stream of carbon dioxide are introduced,
at least one of a refrigerator for the ammonia-containing purge gas, a refrigerator for said stream of carbon dioxide, means to add a refrigerant medium to said mixing device,
the mixing device delivering a multiphase mixed stream containing solid ammonium salts, as a result of mixing and refrigeration of the purge gas and carbon dioxide, and
a phase-separation device disposed to receive said mixed stream from the mixing device and adapted to remove said ammonium salts from said mixed stream.

* * * * *